(12) United States Patent
Steffan et al.

(10) Patent No.: US 8,906,957 B2
(45) Date of Patent: Dec. 9, 2014

(54) POLYPHENOL-RICH EXTRACT FROM PLANT MATERIAL

(75) Inventors: Wolfram Steffan, Bavaria (DE); Kelly Duffin-Maxwell, Boulder, CO (US); Allan Bradbury, Bavaria (DE)

(73) Assignee: Kraft Foods R & D, Inc., Deerfield, IL (US)

( * ) Notice: Subject to any disclaimer, the term of this patent is extended or adjusted under 35 U.S.C. 154(b) by 1329 days.

(21) Appl. No.: 12/443,602

(22) PCT Filed: Oct. 18, 2007

(86) PCT No.: PCT/US2007/081801
§ 371 (c)(1),
(2), (4) Date: Dec. 21, 2009

(87) PCT Pub. No.: WO2008/051799
PCT Pub. Date: May 2, 2008

(65) Prior Publication Data
US 2012/0035252 A1    Feb. 9, 2012

(30) Foreign Application Priority Data
Oct. 20, 2006    (EP) .................................. 06022029

(51) Int. Cl.
*A61K 31/353*    (2006.01)
*A23L 1/30*    (2006.01)

(52) U.S. Cl.
CPC ............. *A23L 1/3002* (2013.01); *A61K 31/353* (2013.01)
USPC ............ 514/456; 426/631; 426/593; 426/594

(58) Field of Classification Search
CPC .......................... A31L 1/3002; A61K 31/353
USPC ........................ 514/456; 426/631, 593, 594
See application file for complete search history.

(56) References Cited

U.S. PATENT DOCUMENTS

| 5,989,557 | A | 11/1999 | Bombardelli et al. | |
|---|---|---|---|---|
| 6,576,275 | B1 * | 6/2003 | Hoving et al. | 424/776 |
| 6,627,232 | B1 | 9/2003 | Hammerstone, Jr. et al. | |
| 2003/0180406 | A1 * | 9/2003 | Sies | 424/776 |
| 2005/0089592 | A1 | 4/2005 | Chevaux et al. | |
| 2006/0052438 | A1 | 3/2006 | Ho et al. | |
| 2006/0269633 | A1 * | 11/2006 | Kopp et al. | 424/776 |
| 2007/0078261 | A1 * | 4/2007 | Robbins et al. | 536/8 |

FOREIGN PATENT DOCUMENTS

| EP | 0 348 781 B1 | 9/1992 |
|---|---|---|
| EP | 0 814 823 B1 | 8/2002 |
| JP | 08-034743 A | 2/1996 |
| JP | 2000060485 A | 2/2000 |
| RU | 2 185 070 C2 | 7/2002 |
| WO | 96/10404 A1 | 4/1996 |
| WO | 98/09533 A1 | 3/1998 |
| WO | 01/45726 A1 | 6/2001 |
| WO | 01/52671 A2 | 7/2001 |
| WO | 2005/107780 A2 | 11/2005 |

OTHER PUBLICATIONS

European Search Report, European Patent Application No. 06022029, date of completion of the search Mar. 22, 2007, 3 pages.
Hideyuki Ito et al., "Polyphenol levels in human urine after intake of six different polyphenol-rich beverages," British Journal of Nutrition (2005), vol. 94, pp. 500-509.

* cited by examiner

*Primary Examiner* — Bong-Sook Baek
(74) *Attorney, Agent, or Firm* — Fitch, Even, Tabin & Flannery LLP

(57) ABSTRACT

A process is provided for preparing (1) a first composition obtained by extracting a plant material with a single phase mixture of water and at least a first organic solvent under agitation so as to obtain a first extract rich in polyphenol oligomers, wherein the first composition is the first extract, and (2) a second composition obtained by extracting at least a portion of the first extract with a biphasic mixture of water and at least a second organic solvent under agitation so as to obtain a second extract rich in polyphenol monomers, dimers, and trimers, wherein the second composition is the second extract. Food products, mendicants, and cosmetics containing the first composition or the second composition are also provided.

14 Claims, 3 Drawing Sheets

POLYPHENOL-RICH EXTRACT FROM PLANT MATERIAL

RELATED APPLICATIONS

The present invention relates to processes for the preparation of polyphenol containing compositions rich in polyphenol oligomers and/or rich in polyphenol monomers, dimers, and trimers. The present invention also relates to compositions obtainable by such processes.

BACKGROUND ART

Polyphenols have gained increasing interest due to their protective effects on human health. In particular, polyphenols were shown to reduce the risk of chronic diseases such as cardiovascular diseases and cancers. Therefore, polyphenols may prove useful in functional foods or as medicines. Their anti-oxidant effect may further lead to applications in cosmetics.

Polyphenols are traditionally known from cocoa beans, but other plants such as sage, green tea, other cocoa products, many other plants and also contain considerable amounts of these natural substances. Due to the increasing demand for natural antioxidants and other health-related products, there is a constant need to explore new raw materials.

Recent studies have shown that the effect of polyphenols varies with their degree of polymerisation (dp). For example, tetramers of procyanidins (dp=4), a special class of polyphenols, proved most effective for ACE inhibition in human umbilical vein endothelial cells (Ottaviani et al., Biochimie 88, 2006, 359-265), tetramers, pentamers and hexamers of procyanidins showed a high inhibitory effect of ACE in isolated rabbit lung cells (Actis-Goretta et al., FEBS Letters 555, 2003, 597-600), and protection from oxidation increases with increasing chain length of procyanidin oligomers (from dp=1 to dp=5) in model liposomes (i.e., procyanidin pentamers show a better liposome protection than procyanidin monomers (Lotito et al., Biochemical and Biophysical Research Communications 276, 2000, 945-951)). Moreover, pentamers of procyanidins inhibited tyrosine kinase ErbB2 expression and decreased cell proliferation in human aortic endothelial cells (Kenny et al., Experimental Biology and Medicine 229, 2004, 255-263). Monomers, dimmers, and trimers of procyanidins, in contrast, have different pharmacokinetic profiles compared to oligomers such as tetramers, pentamers and hexamers of procyanidins.

Osman et al., Food Chemistry 86, 2004, 41-46, describe that consumption of foods and beverages rich in phenolic content can reduce the risk of heart disease, slowing the progression of atherosclerosis by acting as antioxidants towards low-density lipoprotein. Osman et al. also prepared extracts of cocoa leaves and determined their antioxidation potential. However, Osman et al. did not consider procyanidins; it also appears the total polyphenol content obtained by the process applied by Osman et al. was poor.

In JP 2000-060485A, extracts were obtained by extraction with water/hydrochloride for 30 minutes at 90° C. However, procyanidins and their composition were not characterized; it also appears that the total procyanidin content was low. Extraction of procyanidins from cocoa beans is described in U.S. Pat. No. 6,627,232.

However, none of the processes described in the prior art allows regulation of the relative amounts of monomers, dimmers, and trimers in comparison to higher oligomers of procyanidins that show different physiological properties. Additionally, the oligomers appear to have a significantly increased astringent effect as compared to the moners, dimers, and trimers. Moreover, some plant material contains considerable amounts of theobromine that also may cause an increase in bitterness. Processes allowing a reduction of theobromine content would thus be advantageous when plant extracts are used in food.

The challenge of providing a process for preparing polyphenol containing compositions rich in polyphenol oligomers or rich in polyphenol monomers, dimers, and trimers has not yet been solved. Processes that allow the adjustment of the relative content of monomers, dimers and/or trimers and higher procyanidin oligomers (dp=4 to 6) and at the same time reduce the content of theobromine were not known before the present invention.

The present invention provides a process for preparing polyphenol containing compositions rich in polyphenol oligomers and compositions rich in polyphenol monomers, dimers and trimers. The present inventors have developed a process for preparing polyphenol containing compositions that allows for specific adjustment of the content of monomers, dimers and/or trimers and higher procyanidin oligomers. Moreover, present invention significantly reduces the content of theobromine.

DISCLOSURE OF THE INVENTION

In accordance with the present invention, there is provided a process for preparing polyphenol containing compositions comprising a first step of extracting a plant material with a single phase mixture of water and at least a first organic solvent under agitation so as to obtain a first extract rich in polyphenol oligomers. There is also provided a process that further comprises a second step of extracting at least a portion of the first extract with a biphasic mixture of water and at least a second organic solvent under agitation so as to obtain a second extract rich in polyphenol monomers, dimers, and trimers.

One particular embodiment according to the present invention pertains to a process for preparing polyphenol containing compositions comprising a first step of extracting a plant material with a single phase mixture of water and at least a first organic solvent under agitation so as to obtain a first extract rich in polyphenol oligomers and a second step of extracting at least a portion of the first extract with a biphasic mixture of water and at least a second organic solvent under agitation so as to obtain a second extract rich in polyphenol monomers, dimers, and trimers.

A further embodiment of the process for preparing polyphenol containing compositions according to the present invention uses steamed, dried and/or defatted plant material as the starting material.

In an alternative embodiment according to the present invention, the process further comprises the optional step of drying such as freeze drying or spray drying the aqueous solution or suspension obtained by extracting the plant material in the first step.

Moreover, there are also provided polyphenol containing compositions obtainable by these processes as well as food obtainable by incorporating the compositions.

Furthermore, the present invention relates to the use of the compositions as a food ingredient, a medicament, and cosmetics.

The process according to the present invention provides a solution for the above described problem in that it allows specifically adjusting the content of monomers, dimers and/ or trimers and higher procyanidin oligomers and reduces the content of theobromine. The plant material used in the process of the present invention can be any plant material containing polyphenols. In particular, any procyanidin containing plant material can be used. The plant material can be any one of the group consisting of fruit, cereals, beans, nuts, spices, tea, and the like. A particularly preferable class of polyphenols according to the present invention are proanthocyanidins such as procyanidins. "Procyanidins" in the context of the present invention include catechin-based and epi-catechin-based proanthocyanidins as well as catechins. Preferable polyphenols also include polyphenol-0-glycosides (e.g., flavonol-0-glycosides, flavon-0-glycosides), polyphenol-C-glycosides (e.g., flavon-C-glycosides), catechins, N-(hydroxyphenylpropenoyl) L-amino acids, anthocyanins, clovamide, and dideoxyclovamide.

Examples of the forms of fruits that may be used in the present invention include whole fruit, fruit pieces, purees, juices, juice concentrates and mixtures thereof. Examples of fruits includes choke berry, cranberry, blueberry, plum, black currant, strawberry, apple, green grape, goose berry, peach, red currant, and green pear. Cereals include whole or broken grain or flour based materials. Beans include whole or broken beans and related plant material. Cereals and beans include cocoa, cocoa leaves, cocoa pod shells, sumac sorghum, pinto bean, red kidney bean, small red bean and barley. Nuts include hazelnut, pecan, pistachios, almond, and walnut. Spices include cinnamon. Tea includes green tea. Moreover, plant material according to the present invention includes coffee leaves, coffee beans, and coffee berries.

Preferable examples of plant material include cocoa leaves, cocoa pod shells green tea, and coffee leaves. The plant material can be in the form of a powder or in any other suitable form for extraction.

According to the present invention, the plant material is extracted in a first step using a single phase mixture of water and at least a first organic solvent under agitation. The first organic solvent that is used together with water in the single phase mixture according to the process of the present invention can be any organic solvent that is miscible with water. Preferably, the first organic solvent is any one selected from the group consisting of alcohols and ketones. Alcohols according to the present invention include methanol and ethanol. Ketones according to the present invention include acetone and methyl ethyl ketone. Preferably, acetone is used as the first organic solvent in the first step according to the present invention.

The plant material used for the processes according to the present invention can be steamed, dried, and/or defatted. Steaming according to the present invention is carried out by conventional methods using water vapour. Preferably, steaming is carried out for approximately 5 minutes at 98° C. to reduce the polyphenol oxidase activity and thus increase the overall polyphenol yield. Drying is carried out for several hours at elevated temperature, preferably at up to 40° C. The optional step of defatting can be done using a nonpolar solvent. Preferably, nonpolar solvents such as hexane are used for defatting and defatting may be accomplished in a Soxhlet apparatus.

The single phase mixture used in the first step of the process according to the present invention comprises 50 to 80 vol %, preferably 60 to 80 vol % and more preferably 65 to 75 vol % of organic solvent and 20 to 50 vol %, preferably 25 to 40 vol % and more preferably 27 to 35 vol % of water. In a particularly preferable embodiment, the single phase mixture moreover comprises an acid, for example, in an amount of up to 5 vol %, preferably up to 3 vol %. The acid helps to prevent oxidation and polymerization of the procyanidins.

Acids according to the first step of the present invention include any one of formic acid, acetic acid, hydrochloric acid, and phosphoric acid. Acetic acid is a particularly preferable example thereof. The first step of extracting the plant material with the single phase mixture is accomplished at a temperature of between 10 to 60° C., preferably at a temperature of between 20 to 50° C. and more preferably at a temperature of between 35 to 45° C. Moreover, the first step is preferably accomplished at normal pressure for 10 minutes up to 4 hours, preferably for 30 minutes up to 2 hours. The first extract thus obtained can be concentrated by evaporating and/or freeze or spray drying.

The process for preparing polyphenol containing compositions according to the present invention comprising the first step of extracting the plant material with the single phase mixture under agitation results in a first extract that is rich in polyphenol oligomers. Polyphenol oligomers according to the present invention are procyanidin tetramers, pentamers and hexamers (i.e., degree of polymerization of 4 to 6). This first extract that is rich in polyphenol oligomers comprises between 15 and 25 wt %, preferably between 18 and 23 wt % of procyanidin tetramers, between 18 and 30 wt %, preferably between 20 and 25 wt % of procyanidin pentamers and between 10 and 20 wt %, preferably between 11 and 18 wt % of procyanidin hexamers based on the total procyanidin concentration. The first extract that is rich in polyphenol oligomers moreover may comprise up to 10 wt % of procyanidin monomers (i.e., catechin and epicatechin), up to 20 wt % of procyanidin dimers and up to 25 wt % of procyanidin trimers, based on the total procyanidin concentration. In a preferable embodiment, the first extract comprises no more than 3 to 8 wt % of procyanidin monomers, no more than 12 to 19 wt % of procyanidin dimers and no more than 15 to 20 wt % of procyanidin trimers based on the total procyanidin concentration.

According to the present invention, the first extract, or a portion thereof, that is rich in polyphenol oligomers may be extracted with a biphasic mixture of water and at least a second organic solvent under agitation so as to obtain a second extract rich in polyphenol monomers and dimers. The second extract comprises between 10 and 30 wt %, preferably more than 13 wt % of procyanidin monomers, between 20 and 35 wt %, preferably between 23 and 30 wt % of procyanidin dimers as well as between 18 and 28 wt %, preferably between 20 and 25 wt % of procyanidin trimers based on the total procyanidin concentration. Moreover, the second extract may comprise up to 20 wt % of procyanidin tetramers, up to 15 wt % of procyanidin pentamers and up to 10 wt % of procyanidin hexamers based on the total procyanidin concentration. Preferably, the second extract comprises no more than 19 wt % of procyanidin tetramers, no more than 12 wt % of procyanidin pentamers, and no more than 7 wt % of procyanidin hexamers, based on the total procyanidin concentration.

The biphasic mixture of water and at least a second organic solvent that is used according to the present invention in an optional second step of extracting the first extract may comprise any organic solvent that forms a biphasic mixture with water. This second organic solvent is preferably selected from the group consisting of ethyl acetate, dichloromethane, chloroform, diethyl ether, petrol ether, hexane, and mixtures thereof.

The second step of extracting the first extract is accomplished at a temperature of between 10 to 40° C., preferably at a temperature of between 15 to 35° C. and more preferably at a temperature of between 20 to 25° C. Moreover, this second step is preferably accomplished at normal pressure and the volume of the second organic solvent used for extraction is from 0.1 to 3, preferably from 0.2 to 2 and more preferably from 0.3 to 1 based on the volume of the aqueous phase of the biphasic mixture. However, other volume ratios may be applicable depending on the solubility of the polyphenols in the second organic solvent. Extraction can be repeated and the extract thus obtained can be concentrated by evaporating and/or freeze or spray drying.

In other words, there is provided a process for preparing polyphenol containing compositions comprising a first step of extracting a plant material such as cocoa leaves with a single phase mixture of water and at least a first organic solvent under agitation, wherein the single phase mixture may comprise an acid such as acetic acid, so as to obtain a first extract that is enriched in polyphenol oligomers in terms of total polyphenol content. "Enriched in polyphenol oligomers" in the context of the present invention implies that the extract contains more procyanidin oligomers than procyanidin monomers, procyanidin dimers, and procyanidin trimers.

Moreover, there is provided a process that further comprises a second step of extracting the first extract or a portion thereof with a mixture of water and at least a second organic solvent that forms a two phase system with water so as to obtain a second extract that is enriched in procyanidin monomers, dimers and trimers based on the total polyphenol content. "Enriched in polyphenol procyanidin monomers, procyanidin dimers and procyanidin trimers" in the context of the present invention implies that the extract contains more procyanidin monomers, procyanidin dimers and procyanidin trimers than procyanidin oligomers.

Moreover, the second extract shows reduced theobromine contents. In a preferred embodiment according to the present invention, the theobromine content in the second extract is reduced to be only half of the theobromine content of the first extract. In a particularly preferable embodiment according to the present invention, the second extract contains only about a third of the theobromine content contained in the first extract.

The invention also pertains to polyphenol containing compositions obtainable by these processes. Moreover, the invention is also directed to food such as chocolates, cocoa beverages, coffee beverages, cocoa containing products, chocolate containing products, coffee containing products and beverages or refreshments that are obtainable by incorporating these compositions as well as to their use as food ingredient, to their use as a medicament and to their use in cosmetics.

EXAMPLES

Following below, specific embodiments exemplifying the processes and the compositions according to the present invention are presented.

Determination of relative procyanidin oligomer concentration (% of total, normalized). Extracts according to the present invention are concentrated using a parallel evaporator and are purified via solid phase extraction (SPE) on Sephadex LH20 material to separate the target analytes from non-polyphenolic compounds (e.g., sugars and alkaloids). Purified extracts are analysed by means of HPLC, using a normal phase silica column. Analytes are detected using a fluorescence detector. Results are calculated versus external standards (isolated from cocoa beans) and reported in units of mg/100 g. Relative procyanidin oligomer concentrations are then calculated and reported as percentage of the total procyanidin content. This method is generally based on Gu et al., J Agric Food Chem 50, 2002, 4852-4860 and Hammerstone et al., J Agric Food Chem 47, 1999, 490-496.

Determination of polyphenol content according to Folin-Ciocalteau. Polyphenol containing extracts are prepared according to the present invention. The polyphenol content of the extract is determined by reacting the extract with a phosphomolybdic/phosphotungstic acid complex (Folin-Ciocalteau reagent) to form chromogens at basic pH. The blue colored solution is measured photometrically and quantified via an external calibration with a gallic acid standard. Results are expressed as mass percent 'gallic acid equivalents' (GAE) in units of g/100 g. This method is generally described by Singleton et al., Methods in Enzymology (Oxidants and Antioxidants, Part A) 299, 1999, 152-178.

Cocoa leaves. Cocoa leaves were obtained from cocoa plants in Ecuador, transported under moist conditions and used as soon as possible after refrigerated storage. The leaves were steamed for 5 minutes at 98° C., dried overnight at 40° C. and ground using a Retsch grinder (SM 100, three times 2 s at 9000 rpm). Ground leaves were defatted with hexane in a Soxhlet apparatus, cooled down to room temperature and dried in crystallizing dishes.

Preparation of a first extract rich in polyphenol oligomers from Cocoa leaves. Approximately 30 g of defatted cocoa leaf powder were suspended in 500 mL of extraction solvent (acetone/water/acetic acid: 70/29.5/0.5, v/v/v) in a 1 L round flask. The suspension was extracted by agitating the flask at 40° C. for 1 hour at ambient pressure. After filtration, extraction was repeated. The solvents of the combined extracts were removed under reduced pressure at 40° C. using a rotary evaporator. The resultant aqueous solution was freeze dried overnight. The thus obtained first extract was rich in polyphenol oligomers (cf. FIG. 2).

Figure 1:
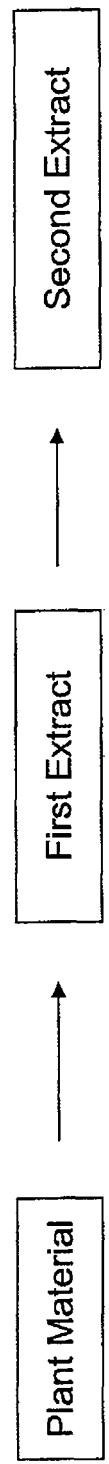
FIG. 1 exemplifies the process for preparing polyphenol containing compositions according to the present invention.
Figure 2:
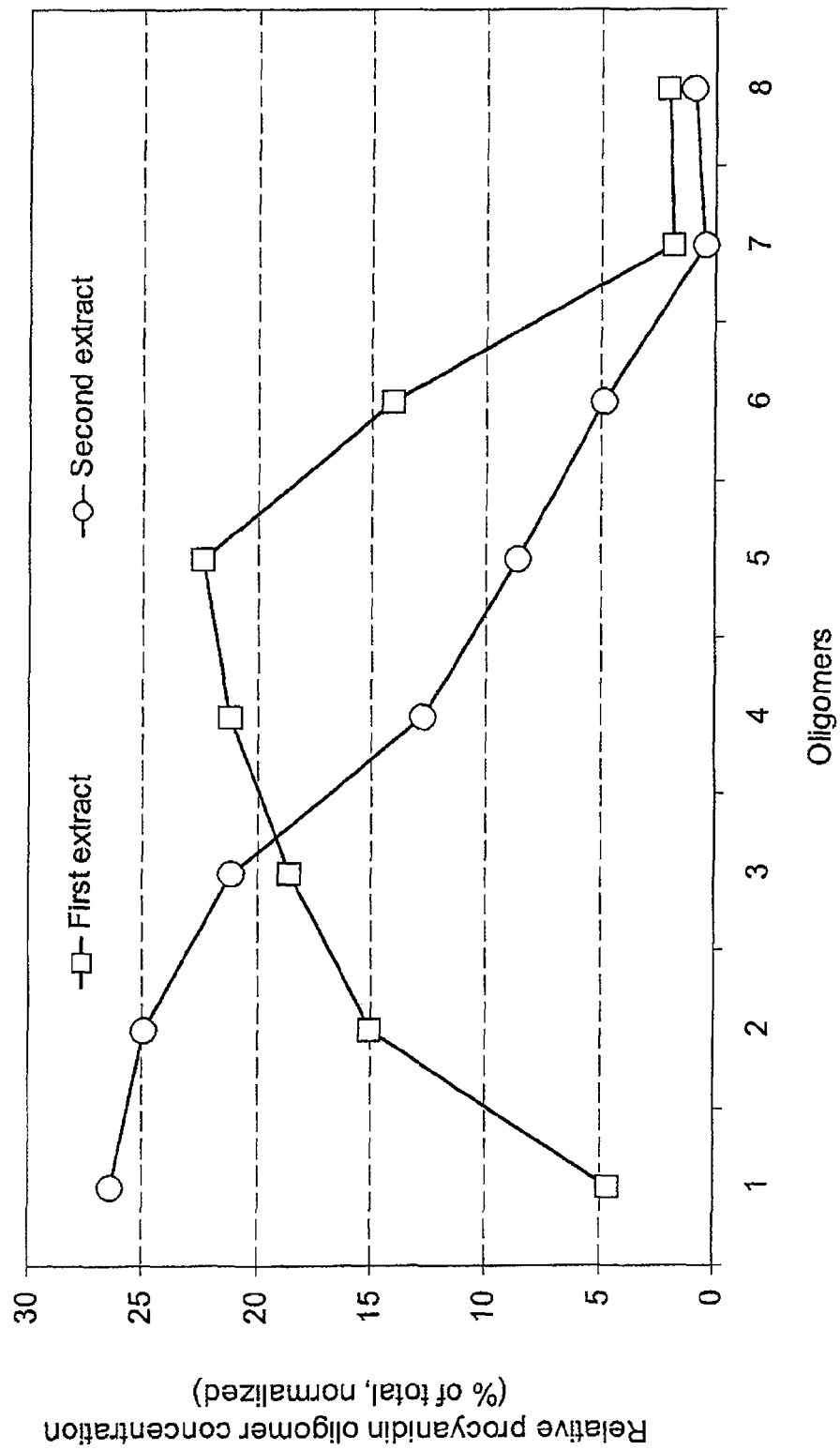
FIG. 2 shows the relative procyanidin polyphenol profiles of cocoa leaves extracts according to the present invention.

Preparation of a second extract rich in polyphenol monomers, dimers and trimers. Approximately 2 g of the first extract were suspended in 500 mL of distilled water in an ultrasonic bath at room temperature. The aqueous suspension was extracted in a partition funnel using ethyl acetate (three times 200 mL). The solvent of the combined organic phases was removed under reduced pressure at 40° C. Distilled water was added to the suspension and freeze dried overnight. The thus obtained second extract had an unexpectedly high polyphenol content of 47 wt % (determined according to Folin-Ciocalteau) comprising 20 wt % procyanidins based on the total polyphenol content. The relative procyanidin profile is shown in FIG. 2.

Cocoa pod shells. Cocoa pods were obtained from cocoa plants in Ecuador, transported under ambient conditions and pod shells were separated from pulp and beans. The pod shells were cut in small pieces, dried for 50 h at 40° C. and ground using a Retsch grinder (SM 100, ten times 5 s at 5000 rpm). Ground cocoa pod shells were defatted with hexane in a Soxhlet apparatus, cooled down to room temperature and dried in crystallizing dishes.

Preparation of a first extract rich in polyphenol oligomers from Cocoa pod shells. Approximately 30 g of defatted cocoa pod shell powder were suspended in 500 mL of extraction solvent (acetone/water/acetic acid: 70/29.5/0.5, v/v/v) in a 1 L round flask. The suspension was extracted by agitating the flask at 40° C. for 1 hour at ambient pressure. After filtration, extraction was repeated. The solvents of the combined extracts were removed under reduced pressure at 40° C. using a rotary evaporator. The resultant aqueous solution was freeze dried overnight. The thus obtained first extract was rich in polyphenol oligomers (cf. FIG. 3).

Figure 3:
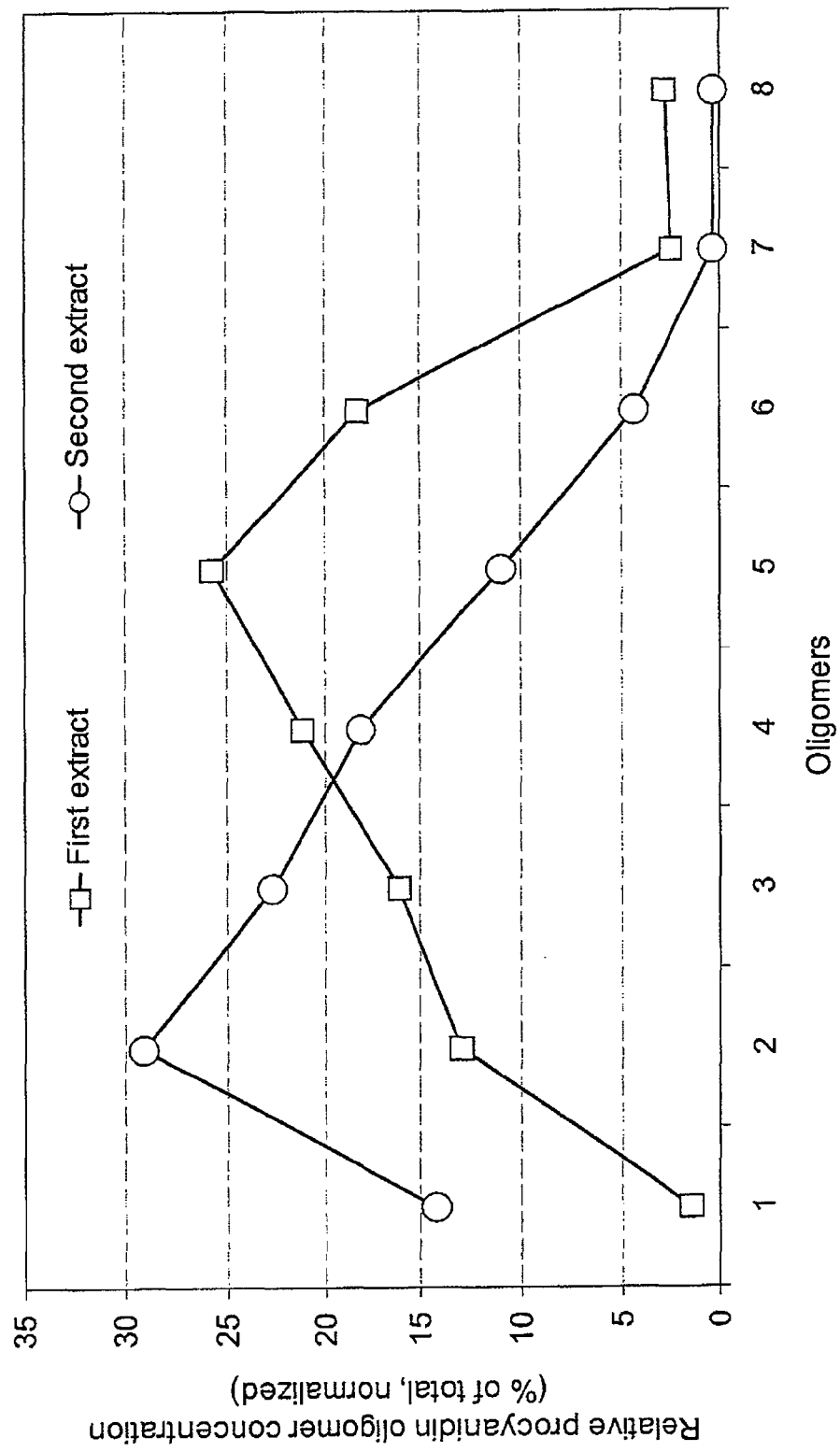
FIG. 3 shows the relative procyanidin polyphenol profiles of cocoa pod shell extracts according to the present invention.

Preparation of a second extract rich in polyphenol monomers, dimers and trimers. The first extract (about 2 g) from the Cocoa pod shells was suspended in 250 mL of distilled water using an ultrasonic bath at room temperature. The aqueous suspension was extracted in a partition funnel using ethyl acetate (three times 100 mL). The solvent of the combined organic phases was removed under reduced pressure at 40° C. Distilled water was added to the suspension and freeze dried overnight. The thus obtained second extract had an unexpectedly high polyphenol content of 49 wt % (determined according to Folin-Ciocalteau) comprising 13 wt % procyanidins based on the total polyphenol content. The relative procyanidin profile is shown in FIG. 3.

The invention claimed is:

1. A process for preparing polyphenol containing compositions, the process comprising:
    extracting a plant material containing theobromine and selected from cocoa leaves, cocoa pod shells, or coffee leaves with a single phase mixture of water and at least one first organic solvent under agitation so as to obtain a first extract rich in polyphenol oligomers, the first extract having less than about 10 wt. % procyanidin monomers, less than about 20 wt. % procyanidin dimers, and less than about 25 wt. % procyanidin trimers based on a total procyanidin concentration;
    extracting at least a portion of the first extract with a biphasic mixture of water and at least one second organic solvent under agitation, separating the second organic solvent phase and removing the second organic solvent so as to obtain a second extract rich in procyanidin monomers, dimers, and trimers, wherein the second extract has a reduced level of the theobromine relative to the plant material, the second extract having about 10-30 wt. % procyanidin monomers, about 20-35 wt. % procyanidin dimers, and about 18-28 wt. % procyanidin trimers based on a total procyanidin concentration; and
    adding the second extract to a food or beverage to form the polyphenol containing composition.

2. The process of claim 1, wherein the first organic solvent is an alcohol or a ketone.

3. The process of claim 2, wherein the single phase mixture further comprises an acid.

4. The process of claim 2, wherein the single phase mixture comprises 50 to 80 vol % of the first organic solvent, 20 to 50 vol % of water, and 0 to 3 vol % of an acid.

5. The process of claim 4, wherein the first organic solvent is methanol, ethanol, acetone, or methyl ethyl ketone.

6. The process of claim 5, wherein the acid is acetic acid.

7. The process of claim 2, wherein the second organic acid is ethyl acetate, dichloromethane, chloroform, diethyl ether, petrol ether, hexane, or mixtures thereof.

8. The process of claim 5, wherein the second organic acid is ethyl acetate, dichloromethane, chloroform, diethyl ether, petrol ether, hexane, or mixtures thereof.

9. The process of claim 1, wherein the plant material is steamed, dried, defatted, or any combination thereof prior to the single phase extraction.

10. The process of claim 8, wherein the plant material is steamed, dried, defatted, or any combination thereof prior to the single phase extraction.

11. The process of claim 1, wherein either or both of the first extract and second extract are freeze dried.

12. The process of claim 8, wherein either or both of the first extract and second extract are freeze dried.

13. The process of claim 1 wherein the first extract comprises about 15 to about 25 wt. % procyanidin tetramers, about 18 to about 30 wt. % procyanidin pentamers, and about 10 to about 20 wt. % procyanidin hexamers based on a total procyanidin concentration.

14. The process of claim 1 wherein the second extract comprises up to about 20 wt. % procyanidin tetramers, up to about 15 wt. % procyanidin pentamers, and up to about 10 wt. % procyanidin hexamers based on a total procyanidin concentration.

* * * * *